(12) United States Patent
Knippelmeyer et al.

(10) Patent No.: US 8,907,277 B2
(45) Date of Patent: Dec. 9, 2014

(54) REDUCING PARTICLE IMPLANTATION

(75) Inventors: Rainer Knippelmeyer, Munich (DE); Nicholas Economou, Lexington, MA (US); Mohan Ananth, Boxborough, MA (US); Lewis A. Stern, Hollis, NH (US); Bill DiNatale, Bedford, MA (US); Lawrence Scipioni, Bedford, MA (US); John A. Notte, IV, Gloucester, MA (US)

(73) Assignee: Carl Zeiss Microscopy, LLC, Thornwood, NY (US)

( * ) Notice: Subject to any disclaimer, the term of this patent is extended or adjusted under 35 U.S.C. 154(b) by 328 days.

(21) Appl. No.: 12/919,676

(22) PCT Filed: Feb. 13, 2009

(86) PCT No.: PCT/US2009/034002
§ 371 (c)(1),
(2), (4) Date: Oct. 21, 2010

(87) PCT Pub. No.: WO2009/114230
PCT Pub. Date: Sep. 17, 2009

(65) Prior Publication Data
US 2011/0049364 A1 Mar. 3, 2011

Related U.S. Application Data

(60) Provisional application No. 61/034,702, filed on Mar. 7, 2008.

(51) Int. Cl.
*H01J 49/00* (2006.01)
*G01N 1/32* (2006.01)

(52) U.S. Cl.
CPC ............ *G01N 1/32* (2013.01); *H01J 2237/0203* (2013.01); *H01J 2237/31749* (2013.01); *H01J 2237/0807* (2013.01)
USPC ...... 250/306; 250/307; 250/492.1; 250/492.3

(58) Field of Classification Search
USPC ............ 250/306, 307, 309, 310, 311, 396 R, 250/397, 396 ML, 492.1, 492.2, 492.3
See application file for complete search history.

(56) References Cited

U.S. PATENT DOCUMENTS 5,093,572 A 3/1992 Hosono
5,969,357 A 10/1999 Todokoro et al.
(Continued)

FOREIGN PATENT DOCUMENTS

EP 1 696 219 8/2006
GB 2 225 156 5/1990
(Continued)

OTHER PUBLICATIONS

Ackermans et al., "Preferential sputtering of B studied by low-energy ion scattering using the dual-isotope surface composition (DISC) method," Surface Science, 227(3):361-368, 1990.
(Continued)

*Primary Examiner* — Nicole Ippolito
*Assistant Examiner* — Hanway Chang
(74) *Attorney, Agent, or Firm* — Fish & Richardson P.C.

(57) ABSTRACT

Methods disclosed herein include: (a) forming a channel in a sample, the channel extending one micron or more along a direction oriented at an angle to a surface of the sample; (b) exposing a portion of the sample above the channel to a particle beam to cause particles to leave the surface of the sample; and (c) forming an image of the sample based on particles that leave the surface.

25 Claims, 7 Drawing Sheets

(56) References Cited

U.S. PATENT DOCUMENTS

| | | |
|---|---|---|
| 6,042,736 A | 3/2000 | Chung |
| 6,576,894 B1 | 6/2003 | Doong |
| 6,727,500 B1 | 4/2004 | Berger et al. |
| 7,238,294 B2 | 7/2007 | Koops et al. |
| 7,452,477 B2 | 11/2008 | Koops et al. |
| 7,537,708 B2 | 5/2009 | Koops et al. |
| 8,304,750 B2 | 11/2012 | Preikszas et al. |
| 2004/0033425 A1 | 2/2004 | Koops et al. |
| 2005/0072753 A1 | 4/2005 | Koops et al. |
| 2005/0279952 A1 | 12/2005 | Ishitani et al. |
| 2006/0011867 A1* | 1/2006 | Kidron et al. ............ 250/492.21 |
| 2007/0029479 A1 | 2/2007 | Gignac et al. |
| 2007/0158558 A1 | 7/2007 | Ward et al. |
| 2008/0011718 A1 | 1/2008 | Koops et al. |
| 2009/0078867 A1* | 3/2009 | Avinun-Kalish et al. ..... 250/309 |
| 2010/0294930 A1 | 11/2010 | Preikszas et al. |

FOREIGN PATENT DOCUMENTS

| | | |
|---|---|---|
| JP | 63 168946 | 7/1988 |
| TW | 200801531 A1 | 1/2008 |
| TW | 200807598 A1 | 2/2008 |
| WO | WO 2009/077450 | 6/2009 |

OTHER PUBLICATIONS

Peisach et al., "Enhanced X-ray yields in PIXE analysis of some binary metal fluorides," Nucl. Instr. and Methods in Phys. Res., 75(14):14-16, 1993.

Pillay et al., "The Application of High Energy Prompt Gamma-Ray Spectrometry to the activation analysis of Light Elements," Nucl. Instr. & Meth. in Phys. Res., B66(1/02):43-47, 1992.

Reyntjens et al., "A review of focused ion beam applications in microsystem technology; Focused ion beam applications in microsystem technology," J. Micromechanics & Microengineering, Inst. of Phys., 11(4):287-300, 2007.

International Search Report and Written Opinion dated Oct. 9, 2009, for corresponding PCT Application No. PCT/US2009/034002.

Moutanabbir and Terreault, "Effects in synergistic blistering of silicon by coimplantation of H, D, and He ions," Applied Physics Letters, 86:051906 (2005).

Taiwanese Office Action and Search Report, with translation thereof, for TW Appl No. 098105873, dated Apr. 24, 2014.

* cited by examiner

REDUCING PARTICLE IMPLANTATION

CROSS-REFERENCE TO RELATED APPLICATIONS

This application is a continuation of, and claims benefit under 35 USC 120 to, international application PCT/US2009/034002, filed Feb. 13, 2009, which claims benefit of U.S. Ser. No. 61/034,702, filed on Mar. 7, 2008. Both of these applications are hereby incorporated by reference in their entirety.

TECHNICAL FIELD

This disclosure relates to particle beams and particle implantation in samples.

BACKGROUND

Samples can be exposed to particle beams for a variety of applications, including sample characterization, sample modification, and particle beam characterization. Exposure of a sample to a particle beam can lead to implantation of particles in the sample.

SUMMARY

In one aspect, the disclosure features a method that includes: (a) forming a channel in a sample, the channel extending one micron or more along a direction oriented at an angle to a surface of the sample; (b) exposing a portion of the sample above the channel to a particle beam to cause particles to leave the surface of the sample; and (c) forming an image of the sample based on particles that leave the surface.

In another aspect, the disclosure features a method that includes: (a) forming a channel in a sample having a surface, where the channel extends along a direction normal to the sample surface and where the channel substantially surrounds a portion of the sample in a plane of the sample surface; (b) exposing the portion of the sample to a particle beam to cause particles to leave the sample surface; and (c) forming an image of the sample based on particles that leave the surface.

In a further aspect, the disclosure features a method that includes: (a) forming a plurality of channels in a sample having a surface, where each of the plurality of channels extends along a direction normal to the surface, and where the plurality of channels are positioned to substantially surround a portion of the sample in a plane of the surface; (b) exposing the portion of the sample to a particle beam to cause particles to leave the sample surface; and (c) forming an image of the sample based on particles that leave the surface.

In another aspect, the disclosure features a method that includes: (a) forming first and second channels in a sample, the first channel extending along a direction oriented at an angle to a first surface of the sample, the second channel extending along a direction normal to the first surface of the sample and having a maximum width in a direction parallel to the first surface of one micron or less; (b) directing a particle beam to be incident on a second surface of the sample to cause particles to leave the second surface, the second surface being positioned between the first and second channels and forming a wall of the first channel; and (c) forming an image of the sample based on particles that leave the second surface.

In a further aspect, the disclosure features a method that includes exposing a sample to a particle beam that includes $^3$He$^+$ ions to cause particles to leave a surface of the sample, and forming an image of the sample based on particles that leave the surface.

In another aspect, the disclosure features a method that includes: (a) exposing a sample to a particle beam to cause particles to leave a surface of the sample, and forming an image frame based on particles that leave the surface; (b) repeating the exposing and detecting to form a plurality of image frames; and (c) combining the image frames to form an image of the sample, where the image frames are combined according to weighting values assigned to each image frame, the weighting value for each frame being determined according to an estimate of accumulated sample damage when the frame is formed.

In a further aspect, the disclosure features a method that includes exposing a surface of a sample to particles, the sample having a channel so that at least some of the particles pass through a portion of the sample and enter the channel.

In another aspect, the disclosure features a method that includes: (a) exposing a surface of a sample to a particle beam to cause particles to leave the surface of the sample, and forming an image of the sample based on particles that leave the surface; and (b) heating the sample during the exposure to the particle beam.

Embodiments of the methods can include one or more of the following features.

The angle can be 45 degrees or less.

Forming the channel can include exposing the sample to a second particle beam that removes material from the sample. The second particle beam can be a gallium ion beam.

The methods can include heating the sample to a temperature of 300° C. or more during exposure of the sample to the particle beam. The sample can be heated with a resistive heating element that contacts the sample. Alternatively, or in addition, the sample can be exposed to a laser beam to heat the sample during exposure of the sample to the particle beam. Alternatively, or in addition, the sample can be exposed to an electron beam to heat the sample during exposure of the sample to the particle beam.

The methods can include adjusting an average energy of the particle beam so that particles that are incident on the portion of the sample pass through the sample and into the channel.

The methods can include, prior to exposing the sample to the particle beam, forming a second channel in the sample, the second channel extending along a direction normal to the surface of the sample and having a maximum width in a direction parallel to the surface of the sample of one micron or less, where the exposed portion of the sample is positioned between the first and second channels. The maximum width of the second channel can be 500 nm or less.

Exposing the portion of the sample to the particle beam can include determining a side length $F \cdot \sqrt{A}$ of a smallest square that encloses the portion of the sample, where A is an area of the portion and F is a constant, and exposing each of M regions of the portion of the sample to the particle beam, where each of the M regions is exposed continuously to the particle beam for a time period $t_1$, a shortest time period between successive exposures of any one of the M regions to the particle beam is $t_2$, and the time periods $t_1$ and $t_2$ are selected so that a ratio $$\frac{t_1}{t_1 + t_2}$$

is less than $$\frac{1}{2F\sqrt{M}}.$$

For example, the ratio $$\frac{t_1}{t_1 + t_2}$$

can be less than $$\frac{1}{4F\sqrt{M}}.$$

The particle beam can include noble gas ions. Alternatively, or in addition, the particle beam comprises gallium ions. The particle beam can include helium ions (e.g., $^3$He$^+$ ions). The methods can include, prior to exposing the portion of the sample to the particle beam, implanting particles that include hydrogen in the portion of the sample. Implanting particles that include hydrogen can include exposing the portion of the sample to a particle beam that includes at least one of hydrogen atoms, hydrogen molecules, and hydrogen ions. A concentration of the implanted particles that include hydrogen in the portion of the sample can be $1.0 \times 10^{15}$ cm$^{-2}$ or more.

The particles that leave the surface of the sample can include one or more particles selected from the group consisting of secondary electrons, scattered primary ions, secondary ions, neutral atoms, and photons.

A maximum width of the channel measured in a direction parallel to the surface of the sample can be one micron or less.

The methods can include adjusting an average energy of the particle beam so that particles that are incident on the second surface pass through the sample and into the second channel.

The particle beam can be an ion beam.

The particles can include ions.

The methods and systems disclosed herein can include one or more of the following advantages.

In some embodiments, reducing particle implantation in the sample can yield sample images which show greater detail than images obtained from samples with larger numbers of implanted particles. Larger numbers of implanted particles can distort surfaces of the sample by causing bubble formation within the sample, for example. Distorted sample surfaces can producing imaging artifacts that result from, for example, local variations in the slope of sample surfaces due to sample swelling and/or bubble formation. As a result, images of the distorted sample surfaces can include variations in image intensity which arise from the local variations in surface slope. By reducing particle implantation, induced variations in the sample surface can be reduced or eliminated, so that sample images include fewer imaging artifacts.

In certain embodiments, reducing particle implantation can help to reduce or avoid sample damage due to exposure of the sample to a particle beam. Particle implantation as a result of exposure to a particle beam can lead to swelling and/or bubble formation and bursting, which can ultimately lead to sample destruction, particularly when the sample is a semiconductor device. By reducing particle implantation, sample destruction can be avoided, and non-destructive sample inspection and/or measurement methods based on particle beam exposure can be implemented in environments such as device fabrication facilities.

In some embodiments, reducing particle implantation enables the use of particle beams such as ion beams for sample imaging, rather than conventional electron beams. Ion beams can provide a number of advantages relative to electron beams when used to acquire images of samples. These advantages can include, for example, a greater depth of focus, a smaller spot size, higher resolution, higher secondary electron yield, and different imaging modalities (e.g., sample imaging based upon backscattered ions). Sample images that are measured following exposure to an ion beam can therefore be of higher quality than images measured following electron beam exposure, and images based on ion beam exposure can include information that is not available or more poorly resolved in corresponding electron beam-based sample images.

The details of one or more embodiments are set forth in the accompanying drawings and description. Other features and advantages will be apparent from the description, drawings, and claims.

DESCRIPTION OF DRAWINGS

Like reference symbols in the various drawings indicate like elements.

DETAILED DESCRIPTION

Figure 1:
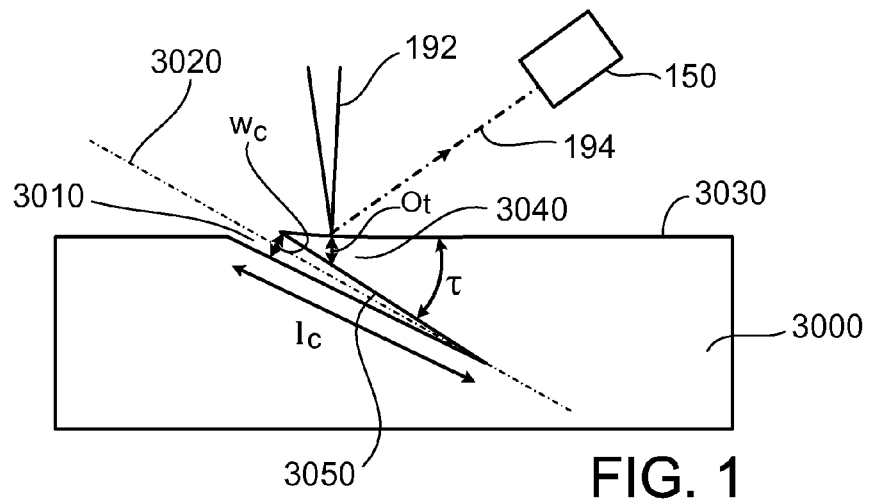
FIG. 1 is a schematic diagram of an embodiment that includes a sample having a channel extending along a direction at an angle to a sample surface.

Exposure of certain materials to particle beams can lead to particle implantation within the materials. In this disclosure, the discussion will focus on particle beams that include helium (e.g., helium ion beams). However, the systems and methods disclosed herein can be used for a wide variety of particle beams, including neutral atom particle beams, and ion beams that include one of more of gallium ions, helium ions, neon ions, argon ions, krypton ions, xenon ions, and other types of ions. In general, the threshold particle dose at which implantation begins to occur depends upon a number of factors, including the material, the nature of the incident particles (e.g., helium ions, and/or other noble gas ions), the incident particle energies, and the incident particle currents.

For some samples, exposure to a helium ion beam can lead to implantation of helium. At sufficiently high doses of helium ions, the implanted helium can form bubble-like cavities beneath the surface of the sample, leading to sample swelling and deformation of the sample surface. If the implanted concentration of helium is sufficiently high, the sub-surface cavities can burst, producing irreversible modifications to the sample surface. For samples that include functional elements (e.g., semiconductor circuit devices), such irreversible modifications can render the functional elements inoperable.

For samples formed of certain materials (e.g., silicon), ion doses from helium ion (and other ion) beams that are used for sample imaging can be high enough to initiate the types of sample distortion and/or damage discussed above. Accordingly, images of the sample that are acquired based upon exposure of the sample to a helium ion beam can include image information that is distorted and/or inaccurate due to the disruptive effects of ion implantation within the sample during imaging.

Disclosed herein are methods and systems for reducing particle (e.g., helium) implantation within samples that are exposed to particle beams (e.g., helium ion beams), so that the disruptive effects of particle implantation can be mitigated. The first part of this disclosure discusses these methods and systems. The second part of this disclosure discusses helium ion beam systems and methods for sample imaging.

I. Reducing Particle Implantation During Ion Beam Exposure

In some embodiments, particle implantation within a sample can be reduced by forming one or more channels in the sample to permit particles to exit the sample. For example, in certain embodiments, particles can enter and subsequently exit the sample during initial exposure of the sample to an ion beam, and one or more channels can be formed in the sample to permit incident ions to be transmitted through the sample and into the one or more channels. Alternatively, or in addition, particles which have already been implanted within the sample during exposure to the ion beam can diffuse out of the sample and into the one or more channels, reducing the concentration of implanted particles within the sample.

FIG. 1 shows an embodiment that includes a channel 3010 which has been formed in a sample 3000. A central axis 3020 extends along channel 3010, and is oriented at an angle τ to surface 3030 of sample 3000. Channel 3010 has a length $l_c$ measured along axis 3020, and a maximum width $w_c$ measured in a direction perpendicular to axis 3020.

Channel 3010 is formed in sample 3000 prior to exposing sample 3000 to helium ion beam 192. Channel 3010 can be formed via a variety of methods. For example, in some embodiments, channel 3010 can be formed by exposing sample 3000 to a particle beam different from helium ion beam 192. In FIG. 1, a particle beam that was incident on sample 3000 in a direction parallel to axis 3020 removed material from sample 3000 to form channel 3010. Particle beams that are suitable for removing material from sample 3000 to form channels can include gallium ion beam, for example.

In certain embodiments, channel 3010 can be formed using other methods. For example, laser ablation can be used to form channels in sample 3000. Alternatively, or in addition, beam-induced chemical etching can be used to form channels such as channel 3010. In beam-induced chemical etching, a beam (e.g., an ion beam, an electron beam, or a beam of electromagnetic radiation) is incident on sample 3000, and one or more chemical agents are introduced in the vicinity of the incident beam to cause etching of the sample. Protective masks can be used during etching steps to selectively etch only certain portions of sample 3000 such as, for example, portions that correspond to channels (e.g., channel 3010) in the sample.

In some embodiments, the angle τ between axis 3020 of channel 3010 and surface 3030 of sample 3000 can be five degrees or more (e.g., 10 degrees or more, 15 degrees or more, 20 degrees or more, 25 degrees or more, 30 degrees or more, 40 degrees or more, 50 degrees or more, 60 degrees or more, 70 degrees or more, 80 degrees or more). Alternatively, or in addition, the angle τ can be between 10 degrees and 80 degrees (e.g., between 15 degrees and 70 degrees, between 15 degrees and 60 degrees, between 15 degrees and 40 degrees).

In certain embodiments, the length $l_c$ of channel 3010 can be 20 nm or more (e.g., 40 nm or more, 60 nm or more, 80 nm or more, 100 nm or more, 200 nm or more, 400 nm or more, 600 nm or more, 800 nm or more, 1 micron or more, 2 microns or more, 5 microns or more, 10 microns or more, 20 microns or more, 30 microns or more). Alternatively, or in addition, $l_c$ can be 500 microns or less (e.g., 400 microns or less, 300 microns or less, 200 microns or less, 100 microns or less, 50 microns or less).

In some embodiments, the maximum dimension $w_c$ of channel 3010 can be 10 nm or more (e.g., 20 nm or more, 30 nm or more, 50 nm or more, 100 nm or more, 200 nm or more, 300 nm or more), and/or 1 micron or less (e.g., 800 nm or less, 600 nm or less, 500 nm or less, 400 nm or less).

After channel 3010 is formed in sample 3000, the portion of sample 3000 that is positioned above channel 3010 (e.g., portion 3040 in FIG. 1) can be imaged by exposing portion 3040 to a helium ion beam. For example, helium ion beam 192 can be directed to be incident on surface 3030 in portion 3040. In response to the incident helium ion beam, particles 194 leave surface 3030 in portion 3040, and can be detected by detector 150. One or more images of sample 3000 (and in particular, of portion 3040) can be acquired based on detected particles 194.

Particles 194 can include, for example, secondary electrons, scattered primary ions, scattered neutral atoms, secondary ions from portion 3040, secondary neutral atoms from portion 3040, and photons. One or more of these different types of particles can be detected to form images of portion 3040. Each of these different types of particles is discussed in more detail in part II of this disclosure.

To reduce implantation of helium in portion 3040 during exposure of portion 3040 to helium ion beam 192, the average energy of the helium ions can be adjusted so that, on average, the incident helium ions are transmitted through portion 3040. That is, the incident helium ions enter portion 3040 through surface 3030, and have sufficient kinetic energy to traverse the entire thickness of portion 3040 and then enter channel 3010 by leaving portion 3040 through back-side surface 3050. The selection of a suitable average energy of the incident helium ions can be made according to various factors, including the material from which sample 3000 is formed and the thickness of portion 3040 through which the ions pass between surfaces 3030 and 3050. By adjusting the incident helium ion energy to allow the ions to be transmitted through portion 3040, the concentration of implanted helium within portion 3040 can be lower than a concentration which would result in the absence of channel 3010. As a result, sample distortion and potential destruction on account of implanted helium can be mitigated.

In general, incident ions in helium ion beam 192 pass through a region of portion 3040 that has a maximum thickness $o_t$, measured along a direction normal to a plane of surface 3030, as shown in FIG. 1. In certain embodiments, $o_t$ is 10 nm or more (e.g., 20 nm or more, 30 nm or more, 40 nm or more, 50 nm or more, 100 nm or more, 500 nm or more) and/or 20 microns or less (e.g., 15 microns or less, 10 microns or less, 5 microns or less, 3 microns or less, 2 microns or less, 1 micron or less). By adjusting the position of helium ion beam 192 relative to portion 3040, the thickness of the exposed region of portion 3040 can be carefully selected. Moreover, channel 3010 permits exposure and imaging of very thin regions of portion 3040.

In some embodiments, despite adjustment of the average incident helium ion energy discussed above, some helium particles will be implanted within portion 3040. To encourage the implanted helium particles to diffuse out of portion 3040, the sample can be heated during (and/or following) exposure to the helium ion beam. Because the diffusion rates of implanted particles within portion 3040 are typically temperature-dependent, a higher particle diffusion rate can be achieved by increasing the temperature of sample 3000. For example, sample 3000 can be heated to a temperature of 50° C. or more (e.g., 100° C. or more, 150° C. or more, 200° C. or more, 250° C. or more, 300° C. or more, 400° C. or more, 500° C. or more) during and/or following exposure to ion beam 192.

Typically, diffusion of implanted particles out of sample 3000 will occur in all directions, and by increasing the diffusion rate of implanted particles, the rate at which implanted particles leave sample 3000 through all sample surfaces will increase. By heating sample 3000, the concentration of implanted particles within the sample can be kept below the threshold concentration for sub-surface cavity (e.g., bubble) formation, for example.

Figure 2:
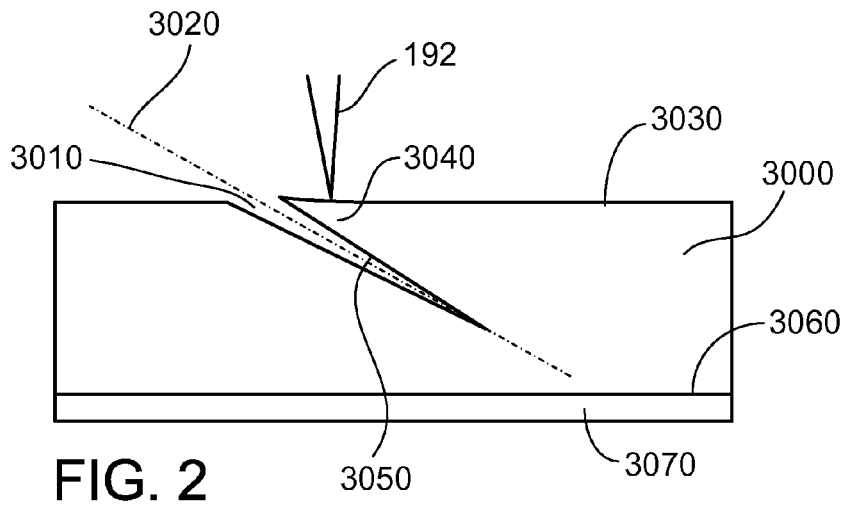
FIG. 2 is a schematic diagram of an embodiment that includes a sample and a resistive heating element contacting the sample.

Various methods can be used to heat sample 3000. In some embodiments, for example, a resistive heating element can be used to increase the temperature of sample 3000. FIG. 2 shows an embodiment where a resistive heating element 3070 contacts a back surface 3060 of sample 3000. The amount of heat energy supplied to sample 3000 can be controlled by varying a voltage applied to heating element 3070, for example.

Figure 12:
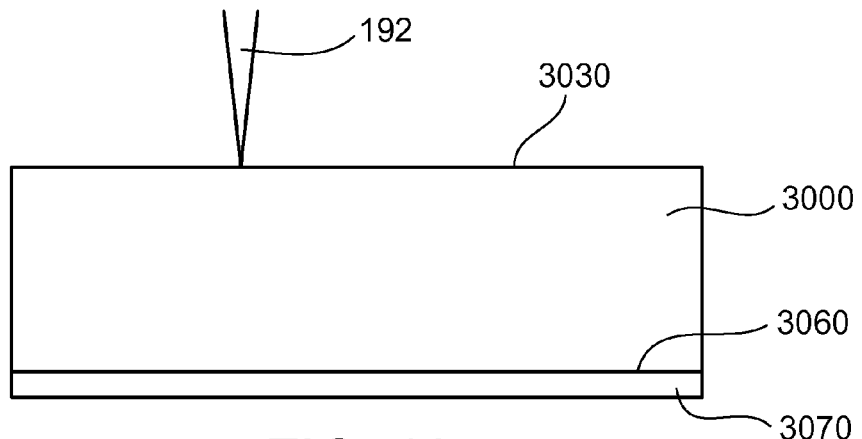
FIG. 12 is a schematic diagram of an embodiment that includes a sample and a heating element that heats the sample.

Although heating element 3070 contacts sample 3000 which has a channel 3010 in FIG. 2, in general, heating elements can contact samples with or without channels to promote diffusion of implanted particles out of the samples. For example, FIG. 12 shows an embodiment in which surface 3030 of sample 3000 is exposed to an ion beam 192. Resistive heating element 3070 contacts surface 3060 of sample 3000. By heating sample 3000 via element 3070, diffusion of implanted particles out of sample 3000 is promoted.

Figure 3:
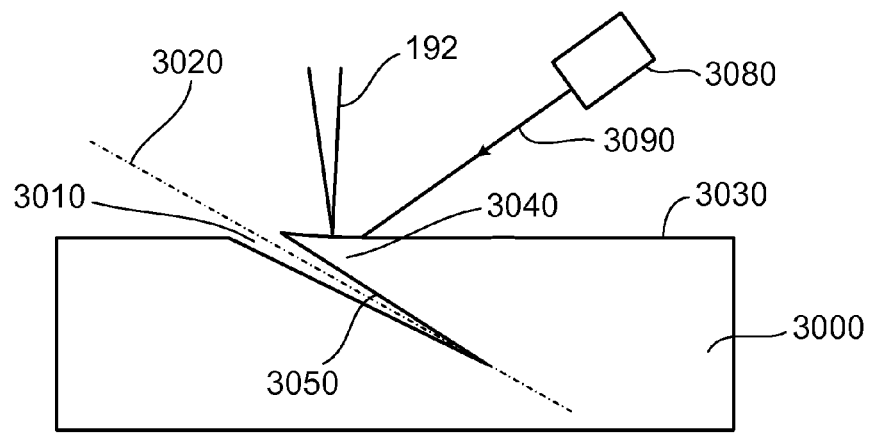
FIG. 3 is a schematic diagram of an embodiment that includes a sample that is exposed to a laser beam to heat the sample.

In certain embodiments, sample 3000 can be exposed to a laser beam to increase the temperature of the sample. FIG. 3 shows an embodiment where a laser 3080 is positioned to direct a laser beam 3090 to be incident on sample 3000 (and in particular, on exposed portion 3040 of sample 3000). Laser beam 3090 delivers electromagnetic energy to sample 3000, which is subsequently converted to thermal energy in the sample, causing the temperature of the sample to increase.

Figure 13:
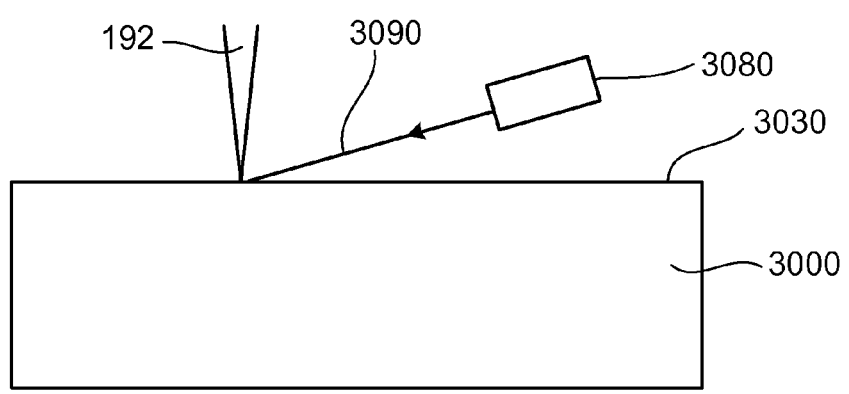
FIG. 13 is a schematic diagram of an embodiment that includes a sample and a laser source that is configured to heat the sample.

Although laser 3080 is used to heat sample 3000 which has a channel 3010 in FIG. 3, in general, laser sources can be used to heat samples with or without channels to promote diffusion of implanted particles out of the samples. For example, FIG. 13 shows an embodiment in which surface 3030 of sample 3000 is exposed to ion beam 192. Laser 3080 is configured to direct laser beam 3090 to be incident on sample 3000 at a position on surface 3030 that is close to ion beam 192. Laser beam 3090 heats sample 3000, promoting diffusion of implanted particles out of sample 3000.

Figure 4:
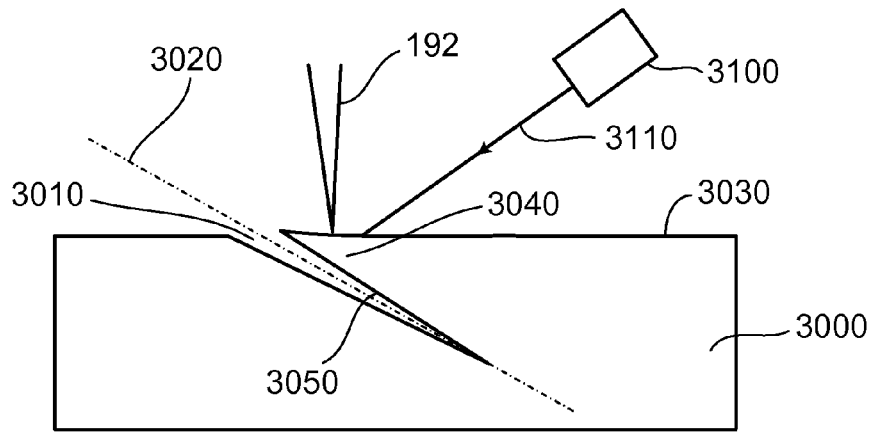
FIG. 4 is a schematic diagram of an embodiment that includes a sample that is exposed to an electron beam to heat the sample.

In some embodiments, sample 3000 can be exposed to an electron beam to increase the temperature of the sample. FIG. 4 shows an embodiment where an electron source 3100 is positioned to direct an electron beam 3110 to be incident on portion 3040 of sample 3000.

Individual electrons in electron beam 3110 have kinetic energy, which is converted to thermal energy in sample 3000 via collisions between the incident electrons and the atoms of sample 3000. As a result, the temperature of sample 3000 increases during exposure to electron beam 3110.

Figure 14:
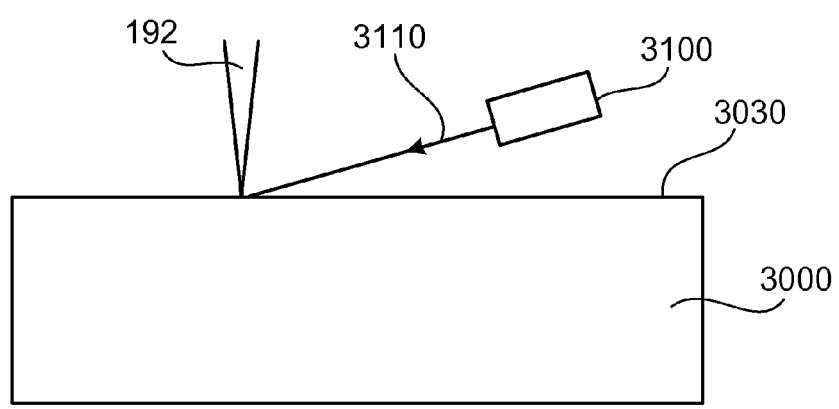
FIG. 14 is a schematic diagram of an embodiment that includes a sample and an electron source that is configured to heat the sample.

Although electron source 3100 is used to heat sample 3000 which has a channel 3010 in FIG. 4, in general, electron sources can be used to heat samples with or without channels to promote diffusion of implanted particles out of the samples. For example, FIG. 14 shows an embodiment in which surface 3030 of sample 3000 is exposed to ion beam 192. Electron source 3100 is configured to direct electron beam 3110 to be incident on sample 3000 at a position on surface 3030 that is close to ion beam 192. Electron beam 3110 heats sample 3000, promoting diffusion of implanted particles out of sample 3000.

Combinations of multiple heating methods can also be used to control the temperature of sample 3000. For example, in certain embodiments, one or more resistive heating elements can be used to heat sample 3000. In addition, sample 3000 can be exposed to a laser beam and/or to an electron beam to further control the temperature of the sample.

In some embodiments, portion 3040 of sample 3000 can be pre-implanted with particles that include hydrogen prior to exposing portion 3040 to helium ion beam 192. In certain materials, pre-implantation with particles that include hydrogen can help to reduce or avoid swelling of the sample, even when relatively high concentrations of helium are subsequently implanted within the sample. To implant particles that include hydrogen within portion 3040, sample 3000 can be exposed to a particle beam that includes at least one of hydrogen atoms, hydrogen ions, hydrogen molecules, and hydrogen-containing molecules, for example.

In certain embodiments, a concentration of the implanted hydrogen-containing particles can be $1.0 \times 10^{14}$ cm$^{-2}$ or more (e.g., $5.0 \times 10^{14}$ cm$^{-2}$ or more, $1.0 \times 10^{15}$ cm$^{-2}$ or more, $5.0 \times 10^{15}$ cm$^{-2}$ or more, $1.0 \times 10^{16}$ cm$^{-2}$ or more, $3.0 \times 10^{16}$ cm$^{-2}$ or more) and/or $1.0 \times 10^{17}$ cm$^{-2}$ or less (e.g., $8.0 \times 10^{16}$ cm$^{-2}$ or less, $6.0 \times 10^{16}$ cm$^{-2}$ or less, $4.0 \times 10^{16}$ cm$^{-2}$ or less).

Suitable systems and methods for pre-implantation of particles that include hydrogen are disclosed, for example, in Moutanabbir and Tumult, "Effects in synergistic blistering of silicon by coimplantation of H, D, and He ions," Applied Physics Letters 86: 051906 (2005), the entire contents of which are incorporated herein by reference.

In some embodiments, specialized ion beam scanning protocols can be used to reduce average concentrations of implanted helium within portion 3040 of sample 3000. For example, exposing certain regions of portion 3040 according to particular protocols can afford additional time for implanted helium to diffuse out of portion 3040 between subsequent exposures, thereby reducing the average concentration of implanted helium in portion 3040. Suitable ion beam scanning protocols are disclosed, for example, in U.S. Provisional Application Ser. No. 61/014,229 entitled "Scanning Charged Particle Beams", filed on Dec. 17, 2007, the entire contents of which are incorporated herein by reference.

In certain embodiments, a band scanning protocol can be used to expose portion 3040 to helium ion beam 192. In some embodiments, a checkerboard scanning protocol can be used to expose portion 3040.

In certain embodiments, portion 3040 can be exposed to helium ion beam 192 according to a generalized scanning protocol, as follows. Under typical operating conditions, a generalized relationship can be established between the time period during which sub-regions of portion 3040 are continuously exposed to ion beam 192, and the time period during which each of the sub-regions is not exposed to the ion beam. This relationship enables implanted helium within portion 3040 to diffuse out of portion 3040 between successive exposures, and thereby permits good quality images of the sample to be obtained.

Figure 5:
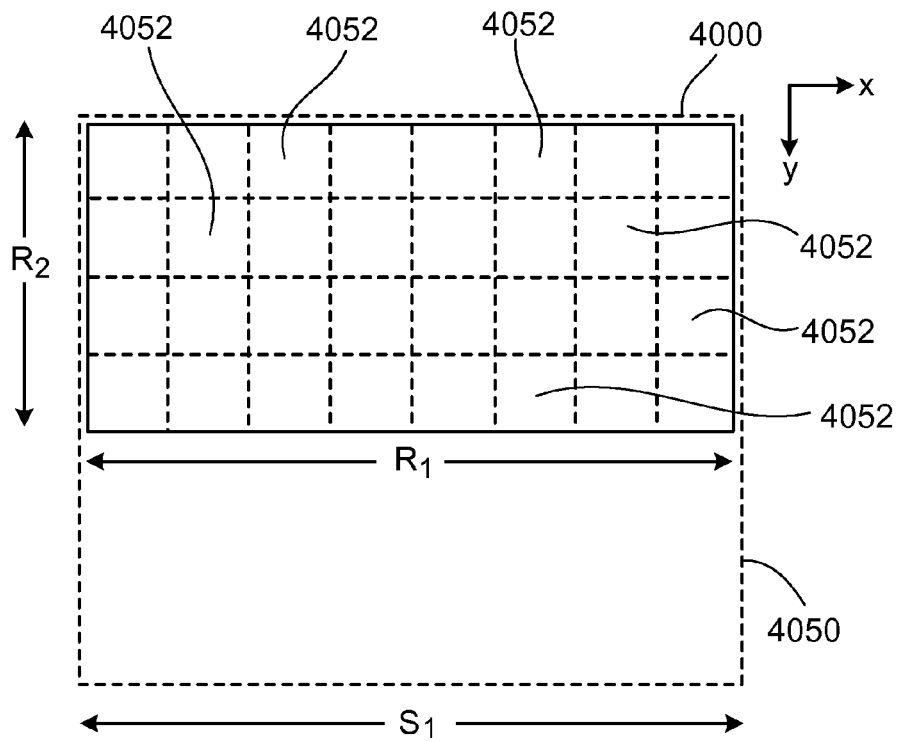
FIG. 5 is a schematic diagram showing a scanning protocol for a sample.

Referring to FIG. 5, a region 4000 (which can correspond to portion 3040 or a sub-portion thereof) of sample 3000 is to be exposed to ion beam 192 to obtain one or more images of the region. Region 4000 is typically a rectangular or square region with length $R_1$ and width $R_2$. To determine the relationship between the continuous exposure and non-exposure times for portions of region 4000, a side length $S_1$ of a square region 4050 is determined, where the square region 4050 corresponds to the smallest square region that fully encloses region 4000. As shown in FIG. 5, determining the side length $S_1$ of square region 4050 for a rectangular or square region 4000 corresponds to determining a maximum dimension (e.g., $R_1$ or $R_2$) of region 4000. Thus, for region 4000 shown in FIG. 5, $S_1 = R_1$. In some embodiments, region 4000 may not be a square region, although in general, determining the side length of square region 4050 will still correspond to determining a maximum dimension of region 4000.

Region 4000 has an area A. The next step in the procedure is to set the side length of square region 4050, $S_1$, equal to the product $F \cdot \sqrt{A}$, where F is a numerical constant that is then easily determined. If region 4000 is a square region, then the value of F will be 1. However, if region 4000 is not square, then F can generally have values other than 1.

Next, region 4000 is divided into a series of M square portions, each of which has the same area and is to be separately exposed to ion beam 192. In general, each of the M portions corresponds to a number of image pixels in images of region 4000. For example, in some embodiments, images of region 4000 include U total pixels, and each of the M portions corresponds to between 4 pixels and U/4 pixels of the image.

Exposure of region 4000 to form a single image frame proceeds as follows. For each of the M portions of region 4000, a subset of the portion is continuously exposed to ion beam 192 for a time period $t_1$. The subset of the portion corresponds to one or more pixels in images of the portion. Then, the ion beam is translated so that a subset of another portion is continuously exposed to the ion beam. Eventually, the ion beam returns to each of the M portions to expose a different subset of each portion (e.g., a subset of each portion which has not already been exposed to the ion beam). The exposing of subsets of portions, followed by translation of the ion beam to other portions, continues until all subsets of each of the portions have been exposed to the ion beam, thereby completing exposure of region 4000 and formation of a single image frame.

In some embodiments, the exposed subsets of each of the M portions correspond to equal numbers of image pixels. In certain embodiments, the exposed subsets correspond to different numbers of image pixels. The M portions can, in some embodiments, be determined according to an approximate interaction volume of incident ions with the material of region 4000. The interaction volume can be measured experimentally and used to determine the number (and therefore, the spacing) of portions M in region 4000. Alternatively, or in addition, the interaction volume of incident ions with the material of region 4000 can be estimated from a database such as a table of measured interaction volumes in particular materials. Once the interaction volume is estimated from such a database, the number and spacing of portions M in region 4000 can be determined.

In some embodiments, the time period between successive continuous exposures of one of the M portions to the ion beam is the same for that one portion, and the same for all M portions of region 4000. More generally, however, the time period between successive continuous exposures of one of the M portions to the ion beam can vary for a given portion, and can vary from portion to portion within region 4000.

As discussed above, the time period $t_1$ corresponds to the time during which any of the M portions (or subsets thereof) are continuously exposed to the ion beam. A time period $t_2$ corresponds to the shortest time period between successive exposures of any of the M portions to the ion beam. For a given region 4000 and number of portions M, the values of $t_1$ and $t_2$ can vary widely according to different exposure protocols. In general, however, the time periods $t_1$ and $t_2$ are selected so that $$\frac{t_1}{t_1 + t_2} \leq \frac{1}{2F} \sqrt{\frac{1}{M}} \quad (1)$$

The equality in Equation (1) represents an upper limit on the value of the ratio $$\frac{t_1}{t_1 + t_2}.$$

In the value of this ratio can be equal to or less than the value shown on the right side of Equation (1). For example, in some embodiments, the value of $$\frac{t_1}{t_1 + t_2}$$

is $$\frac{1}{3F} \sqrt{\frac{1}{M}}$$

or less (e.g., $$\frac{1}{4F}\sqrt{\frac{1}{M}}$$

or less, $$\frac{1}{5F}\sqrt{\frac{1}{M}}$$

or less, $$\frac{1}{10F}\sqrt{\frac{1}{M}}$$

or less, or even less).

Figure 6:
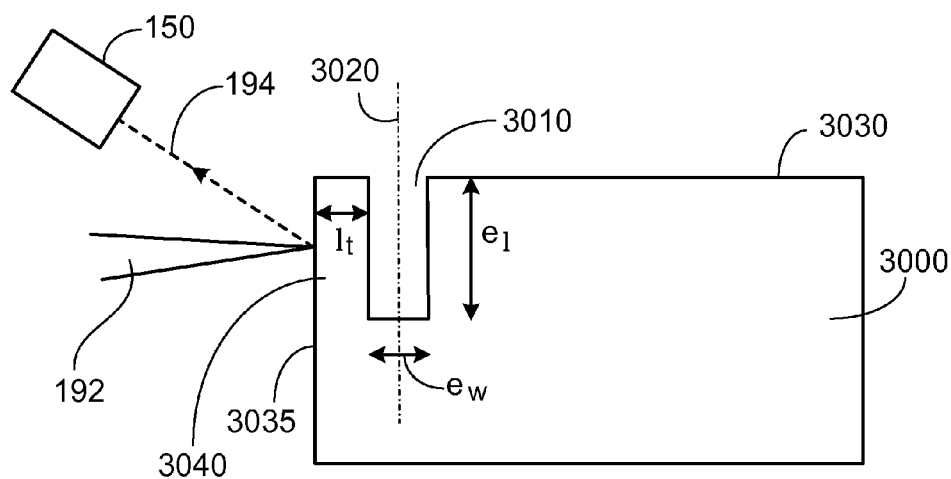
FIG. 6 is a schematic diagram of an embodiment that includes a sample having a channel extending along a direction that is normal to a sample surface.

In some embodiments, the angle τ between axis 3020 of channel 3010 and surface 3030 can be approximately 90 degrees. In other words, channel 3010 can extend into sample 3000 in a direction that is approximately normal to a plane of surface 3030. An embodiment showing channel 3010 extending in this direction is shown in FIG. 6. In FIG. 6, channel 3010 is formed near to an edge of sample 3000, so that a thin, lamellar portion 3040 of sample 3000 is formed. Channel 3010 extends to a depth $e_l$ below surface 3030, and has a maximum width $e_w$ measured in a direction within the plane of surface 3030.

In certain embodiments, the depth $e_l$ of channel 3010 can be 20 nm or more (e.g., 40 nm or more, 60 nm or more, 80 nm or more, 100 nm or more, 200 nm or more, 400 nm or more, 600 nm or more, 800 nm or more, 1 micron or more, 2 microns or more, 5 microns or more, 10 microns or more, 20 microns or more, 30 microns or more). Alternatively, or in addition, $e_l$ can be 500 microns or less (e.g., 400 microns or less, 300 microns or less, 200 microns or less, 100 microns or less, 50 microns or less).

In some embodiments, the maximum width $e_w$ of channel 3010 can be 10 nm or more (e.g., 20 nm or more, 30 nm or more, 50 nm or more, 100 nm or more, 200 nm or more, 300 nm or more), and/or 1 micron or less (e.g., 800 nm or less, 600 nm or less, 500 nm or less, 400 nm or less). By maintaining the maximum width of channel 3010 relatively small, for example, channel 3010 can be formed relatively quickly in sample 3000 prior to sample imaging.

In the embodiment shown in FIG. 6, helium ion beam 192 is incident on portion 3040 from the side. Typically, the average energy of the incident helium ions is adjusted so that the ions are transmitted through portion 3040 and enter channel 3010, reducing or avoiding build-up of implanted helium within portion 3040.

In response to the incident helium ions, one or more types of particles 194 leave surface 3035 of sample 3000, and are detected by detector 150. As discussed above in connection with FIG. 1, particles 194 can include, for example, secondary electrons, scattered primary ions, scattered neutral atoms, secondary ions from portion 3040, secondary neutral atoms from portion 3040, and photons. One or more of these different types of particles can be detected to form images of portion 3040. If sample 3000 includes layers of different materials, images of portion 3040 can correspond to cross-sectional images of sample 3000.

Incident ions in helium ion beam 192 pass through a region of portion 3040 that has a maximum thickness $l_t$, measured along a direction normal to a plane of surface 3035, a shown in FIG. 6. In certain embodiments, $l_t$ is 10 nm or more (e.g., 20 nm or more, 30 nm or more, 40 nm or more, 50 nm or more, 100 nm or more, 500 nm or more) and/or 20 microns or less (e.g., 15 microns or less, 10 microns or less, 5 microns or less, 3 microns or less, 2 microns or less, 1 micron or less). By forming channel 3010 at a particular location relative to surface 3035, the thickness of lamellar portion 3040 (and the exposed region thereof) can be carefully selected. Selectively forming channel 3010 at a particular location relative to 3035 permits exposure and imaging of very thin cross-sections of sample 3000.

The various methods discussed above in connection with FIG. 1 for reducing helium implantation can also be applied in the embodiment shown in FIG. 6. For example, sample 3000 in FIG. 6 can be heated using the methods disclosed to increase the rate of diffusion of implanted helium out of portion 3040. Portion 3040 can be pre-implanted with particles that include hydrogen to mitigate swelling of portion 3040 due to subsequently implanted helium. Specialized scanning protocols can be used to allow additional time for implanted helium to diffuse out of portion 3040 between successive exposures.

Figure 7:
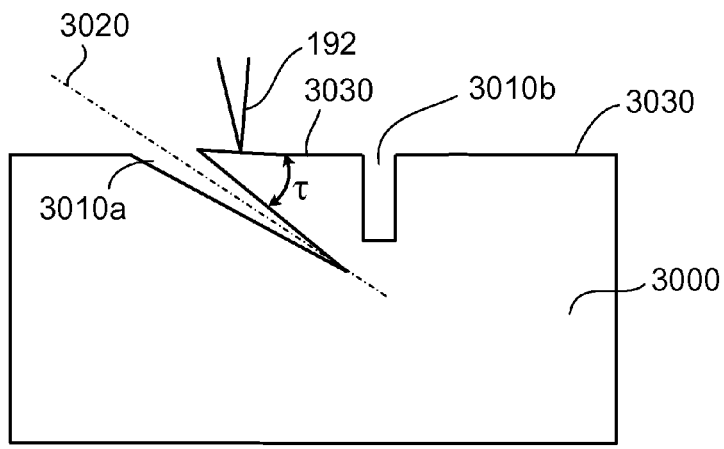
FIG. 7 is a schematic diagram of an embodiment that includes a sample having two channels.

In certain embodiments, channels such as those shown in FIGS. 1 and 6 can both be formed in a sample to provide exit paths for incident ions and/or implanted particles. FIG. 7 shows an embodiment in which two channels, 3010a and 3010b, are formed in sample 3000. Channel 3010a extends along an axis 3020 that is oriented at an angle T to the plane of surface 3030, and channel 3010b extends along a direction normal to the the plane of surface 3030. Portion 3040 of sample 3000, positioned between channels 3010a and 3010b, is exposed to helium ion beam 192. One or more different types of particles leave surface 3030 in portion 3040, and can be detected. Information about the detected particles can be used to form images of portion 3040.

Channel 3010a provides an exit path for incident ions in helium ion beam 192; the average energy of the incident ions can be adjusted so that the incident ions are, on average, transmitted through portion 3040, and enter channel 3010a. Both channels 3010a and 3010b provide exit channels for particles that are implanted within portion 3040, and which can leave portion 3040 by diffusing out of portion 3040 and into either of channels 3010a and 3010b (in addition to leaving portion 3040 through surface 3030).

Figure 8:
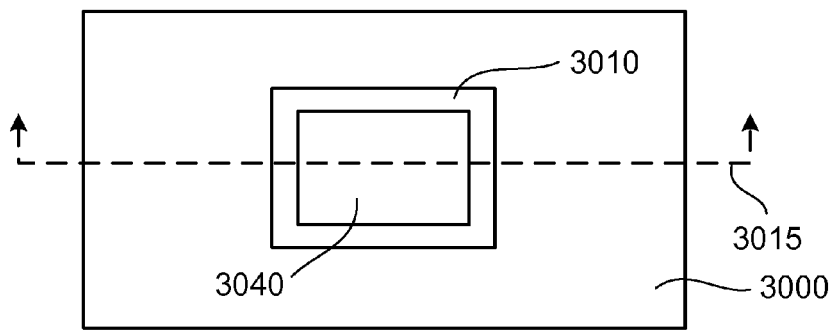
FIG. 8 is a schematic diagram of an embodiment that includes a sample having a channel that surrounds a portion of the sample in a plane of a sample surface.
Figure 9:
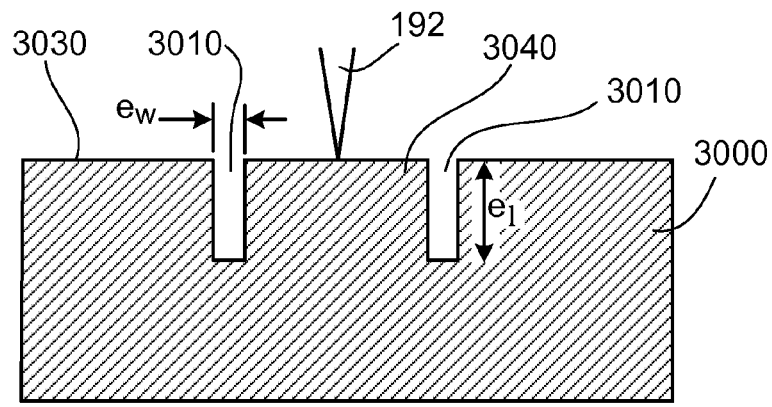
FIG. 9 is a cross-sectional view of the sample of FIG. 8.

In some embodiments, a channel can be formed in a sample which substantially surrounds a portion of the sample that is to be imaged via exposure to the helium ion beam. FIG. 8 shows a top view of an embodiment in which channel 3010 substantially surrounds a portion 3040 of sample 3000 in a plane of surface 3030 of sample 3000. Portion 3040 is essentially an island of material, separated from the remainder of sample 3000 by channel 3010. FIG. 9 is a cross-sectional view of the embodiment shown in FIG. 8 along section line 3015. As shown in FIG. 9, channel 3010 typically extends along a direction normal to the plane of surface 3030, although in general, channel 3010 can extend along any direction relative to the plane of surface 3030, including non-normal directions. The maximum length of channel 3010, measured along a direction normal to the plane of surface 3030, is $e_l$, and the maximum width of channel 3010, measured along a direction in the plane of surface 3030, is $e_w$. These parameters can take any of the values previously disclosed in connection with FIG. 6, for example.

Images of portion 3040 are formed by exposing portion 3040 to helium ion beam 192, and detecting one or more different types of particles that leave surface 3030 of portion 3040 in response to the incident helium ions. Particles that leave surface 3030 can include any of the different types of particles discussed above; information derived from the detected particles is used to form the sample images.

Channel 3010 provides an exit path for particles that are implanted within portion 3040 of sample 3000. Essentially, the rate at which implanted particles leave portion 3040 depends upon the diffusion rate of the implanted particles within portion 3040, and the available surface area of portion 3040 through which the implanted particles can pass to leave portion 3040. Channel 3010 provides additional surface area (e.g., in addition to surface 3030) through which the diffusing, implanted particles can leave portion 3040. The rate at which implanted particles leave portion 3040 is therefore increased by forming channel 3010, which lowers the transient concentration of implanted helium in portion 3040.

Various methods discussed above in connection with FIG. 1 for reducing helium implantation can also be applied in the embodiment shown in FIGS. 8 and 9. For example, sample 3000 in FIGS. 8 and 9 can be heated using the methods disclosed to increase the rate of diffusion of implanted helium out of portion 3040. Portion 3040 can be pre-implanted with particles that include hydrogen to mitigate swelling of portion 3040 due to subsequently implanted helium. Specialized scanning protocols can be used to allow additional time for implanted helium to diffuse out of portion 3040 between successive exposures.

Figure 10:
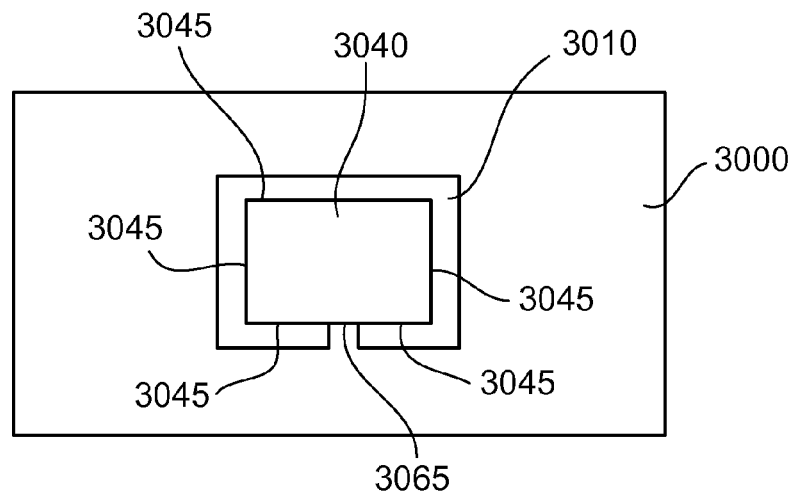
FIG. 10 is a schematic diagram of an embodiment that includes a sample having a channel that substantially surrounds a portion of the sample.
Figure 11:
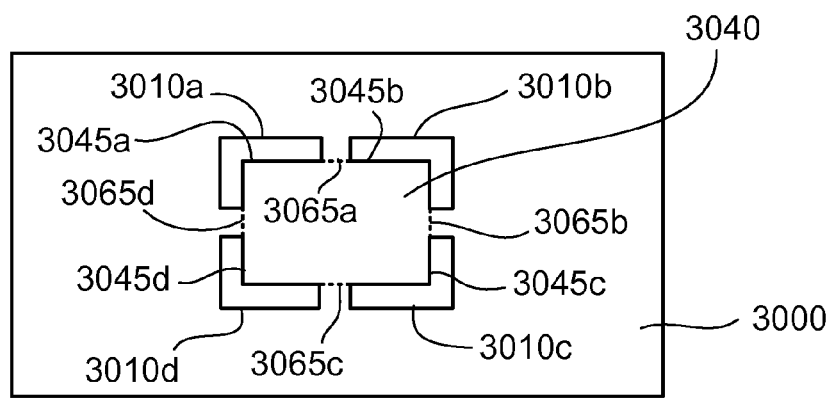
FIG. 11 is a schematic diagram of an embodiment that includes a sample having a plurality of channels that together substantially surround a portion of the sample.

In certain embodiments, channel 3010 does not completely surround portion 3040 in the plane of surface 3030, but substantially surrounds portion 3040 in the plane of surface 3030. For the purpose of this disclosure, channel 3010 substantially surrounds portion 3040 if channel 3010 extends along 75% or more of a perimeter of portion 3040 in the plane of surface 3030. FIG. 10 shows an embodiment where channel 3010 substantially surrounds portion 3040. The perimeter of portion 3040 is formed by wall 3045 of channel 3010, and by line 3065 which connects the discontinuous portions of wall 3045 in a straight line. Because the length of wall 3045 in FIG. 10 is more than 75% of the sum of the length of wall 3045 and line 3065, channel 3010 substantially surrounds portion 3040 of sample 3000. In some embodiments, multiple channels can be formed in sample 3000, and the multiple channels collectively substantially surround portion 3040. FIG. 11 shows an embodiment in which channels 3010a, 3010b, 3010c, and 3010d are formed in sample 3000, and together substantially surround portion 3040 of the sample. The perimeter of portion 3040 is formed by walls 3045a, 3045b, 3045c, and 3045d of the channels, and lines 3065a, 3065b, 3065c, and 3065d which connect the walls. Because the sum of the lengths of walls 3045a, 3045b, 3045c, and 3045d is at least 75% of the sum of the lengths of walls 3045a, 3045b, 3045c, 3045d and lines 3065a, 3065b, 3065c, and 3065d, channels 3010a, 3010b, 3010c, and 3010d together substantially surround portion 3040 of sample 3000.

The arrangement of channels shown in FIG. 11 is exemplary. In general, the number, shape, and position of the multiple channels can vary. In certain embodiments, arrangements of multiple channels do not substantially surround portion 3040 of sample 3000 according to the definition discussed above, while in some embodiments, arrangements of multiple channels do substantially surround portion 3040. A wide variety of different numbers, shapes, and positions of channels can generally be used to substantially surround portion 3040.

Various methods discussed above in connection with FIG. 1 for reducing helium implantation can also be applied in the embodiments shown in FIGS. 8-11. For example, sample 3000 in FIGS. 8-11 can be heated using the methods disclosed to increase the rate of diffusion of implanted helium out of portion 3040. Portion 3040 can be pre-implanted with particles that include hydrogen to mitigate swelling of portion 3040 due to subsequently implanted helium. Specialized scanning protocols can be used to allow additional time for implanted helium to diffuse out of portion 3040 between successive exposures.

In general, portion 3040 of sample 3000 can be exposed to any type of particle beam that causes one or more different types to leave portion 3040, where at least some of the one or more different types of particles are detected and information therefrom is used to form images of sample 3000. In some embodiments, the particle beam that is used to expose portion 3040 is an ion beam that includes one or more different types of noble gas ions. In particular, for example, the particle beam can be a helium ion beam (e.g., helium ion beam 192). In certain embodiments, helium ion beam 192 can include primarily only one type of helium ion isotope, e.g., $^4$He$^+$. In some embodiments, helium ion beam 192 can include more than one type of helium ion isotope, e.g., $^4$He$^+$ and $^3$He$^+$. In certain embodiments, a ratio of the concentration of $^3$He$^+$ to $^4$He$^+$ can be 0.05 or more (e.g., 0.1 or more, 0.2 or more, 0.3 or more, 0.4 or more, 0.5 or more, 0.75 or more, 1.0 or more, 1.5 or more, 2.0 or more, 2.5 or more, 3.0 or more, 5.0 or more, 10.0 or more, 20.0 or more, 50.0 or more). Helium ions $^3$He$^+$ are lighter than $^4$He$^+$ ions, and therefore have higher diffusion rates. Implanted helium in portion 3040 of sample 3000 that is derived from incident $^3$He$^+$ ions will therefore diffuse out of portion 3040 more rapidly than implanted helium that is derived from incident $^4$He$^+$ ions. Therefore, by using larger concentrations of incident $^3$He$^+$ ions in ion beam 192, the transient concentration of implanted helium in portion 3040 of sample 3000 can be reduced.

In some embodiments, sample exposure times and incident ion beam currents can be selected so that images of sample 3000 can be acquired before the onset of sample damage due to particle implantation in the sample. For example, sensitive, high-speed detectors can be used in combination with suitably chosen exposure times and ion beam currents so that even though sample damage occurs, suitable images of the sample have been collected by the time the onset of sample damage is reached.

In certain embodiments, a suitable incident ion beam can be selected based on the material of sample 3000 to reduce the effects of swelling during sample imaging. For example, certain ions that are heavier than helium (e.g., neon and/or argon) can be implanted within certain materials without causing appreciable swelling. The heavier gas ions can have other deleterious effects, such as material sputtering. However, sensitive, high-speed detection electronics can be combined with heavy ion exposure to acquire sample images before the onset of severe sample damage due to sputtering by the incident heavy ions.

In some embodiments, multiple image frames can be formed and combined to produce an image of sample 3000 that is exposed to helium ion beam 192. A portion of sample 3000 (such as, for example, portion 3040) can be exposed multiple times to helium ion beam 192, so that during each exposure, one or more different types of particles leaving the exposed portion are detected, and information therefrom is used to form an image frame of the sample. Exposure of the portion of the sample can be repeated, each time followed by formation of another image frame. Repeated exposure of the sample to the helium ion beam can lead to helium implantation and distortion and/or damage to the sample. However, if such sample distortion and/or damage occurs, the resulting inaccuracy in image data is likely to manifest more strongly in later-acquired image frames, where repeated exposure of the sample can lead to accumulation of implanted helium. Accordingly, to form an image of the sample, the multiple image frames can be combined according to weighting values which discount the values in later-acquired image frames relative to the values in earlier-acquired image frames.

In particular, for example, the weighting values that are applied to each of the image frames can be determined according to estimates of accumulated sample damage at the time each image frame is formed. In certain embodiments, weighting values for each image frame can be determined manually by a system operator based on visual inspection of the image frames. In some embodiments, weighting values for each image frame can be determined automatically based on one or more parameters that are determined for each image frame based on the data values in the image frame. Suitable parameters can include, for example, an intensity variance within each frame, an average intensity within each frame, and changes in image intensity among selected spatial regions of each frame.

In general, the methods discussed above can be combined to further reduce implantation of particles in the sample. For example, the disclosed channels can be formed alone or in combination with one another. A sample that includes any arrangement of one or more channels can be heated using any of the various methods disclosed herein to increase the diffusion rate of implanted particles out of the sample. Particles that include hydrogen can be pre-implanted into portions of the sample that are to be exposed to the helium ion beam to reduce sample swelling. Specialized scanning protocols can be used with longer intervals between successive exposures of the sample, to allow for greater diffusion of implanted particles out of the sample than would otherwise occur with standard scanning protocols. Helium ion beams that include significant concentrations of $^3\text{He}^+$ ions can be used to expose the sample, given the higher diffusion rates of implanted particles derived from $^3\text{He}^+$ ions relative to the diffusion rates of implanted particles derived from $^4\text{He}^+$ ions. Frame averaging techniques can be used to form sample images from multiple image frames, where later-acquired frames can be weighted less heavily than earlier-acquired frames to account for inaccurate image data that can appear in later-acquired frames due to accumulated implanted particles in the sample.

II. Ion Beam Systems

This section discloses systems and methods for producing ion beams, and detecting particles including secondary electrons that leave a sample of interest due to exposure of the sample to an ion beam. The systems and methods can be used to obtain one or more images of the sample.

Typically, gas ion beams that are used to interrogate samples are produced in multipurpose microscope systems. Microscope systems that use a gas field ion source to generate ions that can be used in sample analysis (e.g., imaging) are referred to as gas field ion microscopes. A gas field ion source is a device that includes an electrically conductive tip (typically having an apex with 10 or fewer atoms) that can be used to ionize neutral gas species to generate ions (e.g., in the form of an ion beam) by bringing the neutral gas species into the vicinity of the electrically conductive tip (e.g., within a distance of about four to five angstroms) while applying a high positive potential (e.g., one kV or more relative to the extractor (see discussion below)) to the apex of the electrically conductive tip.

Figure 15:
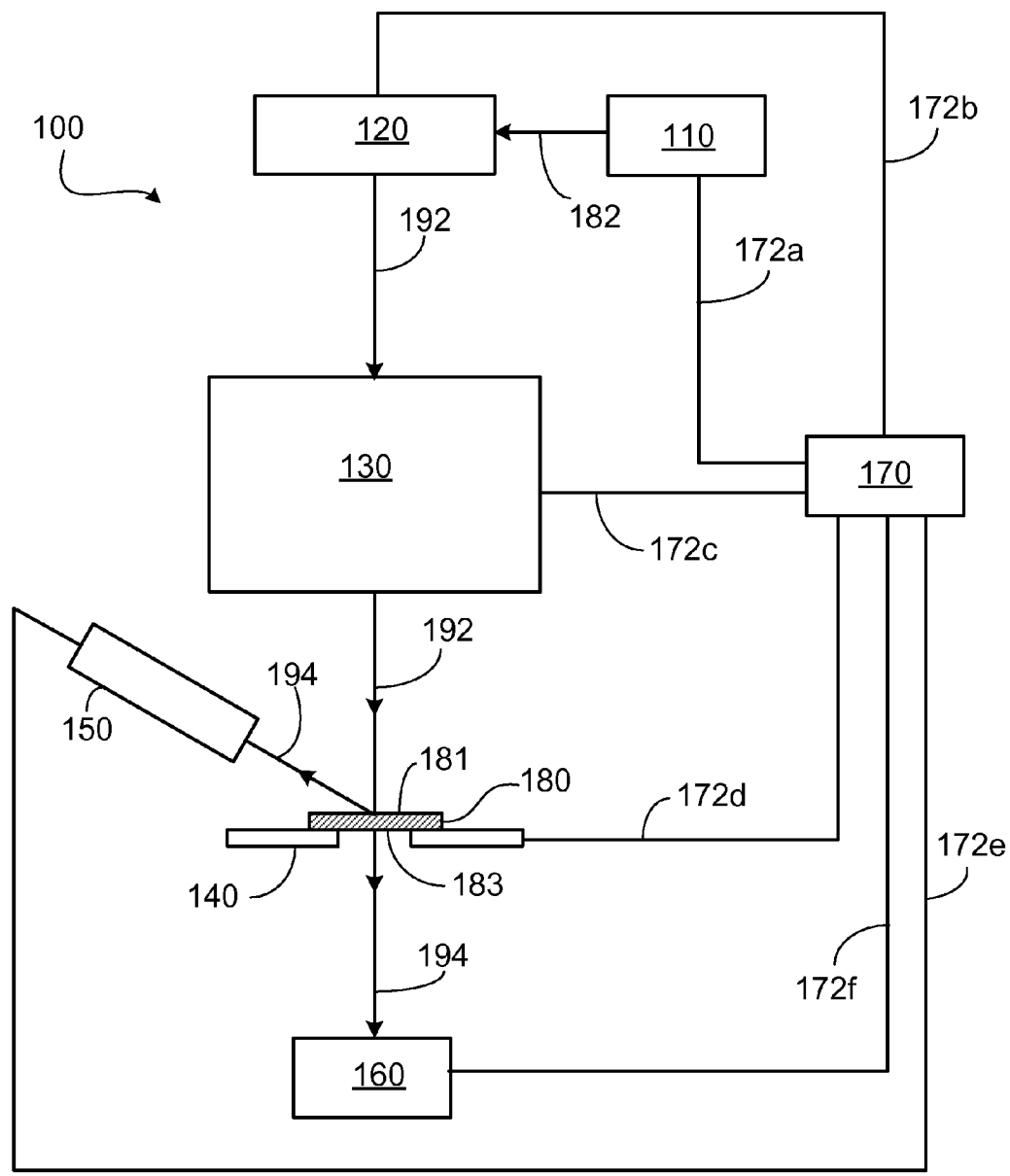
FIG. 15 is a schematic diagram of an ion microscope system.

FIG. 15 shows a schematic diagram of a gas field ion microscope system 100 that includes a gas source 110, a gas field ion source 120, ion optics 130, a sample manipulator 140, a front-side detector 150, a back-side detector 160, and an electronic control system 170 (e.g., an electronic processor, such as a computer) electrically connected to various components of system 100 via communication lines 172a-172f. A sample 180 is positioned in/on sample manipulator 140 between ion optics 130 and detectors 150, 160. During use, an ion beam 192 is directed through ion optics 130 to a surface 181 of sample 180, and particles 194 resulting from the interaction of ion beam 192 with sample 180 are measured by detectors 150 and/or 160.

In general, it is desirable to reduce the presence of certain undesirable chemical species in system 100 by evacuating the system. Typically, different components of system 100 are maintained at different background pressures. For example, gas field ion source 120 can be maintained at a pressure of approximately $10^{-10}$ Torr. When gas is introduced into gas field ion source 120, the background pressure rises to approximately $10^{-5}$ Torr. Ion optics 130 are maintained at a background pressure of approximately $10^{-8}$ Torr prior to the introduction of gas into gas field ion source 120. When gas is introduced, the background pressure in ion optics 130 typically increase to approximately $10^{-7}$ Torr. Sample 180 is positioned within a chamber that is typically maintained at a background pressure of approximately $10^{-6}$ Torr. This pressure does not vary significantly due to the presence or absence of gas in gas field ion source 120.

Figure 16:
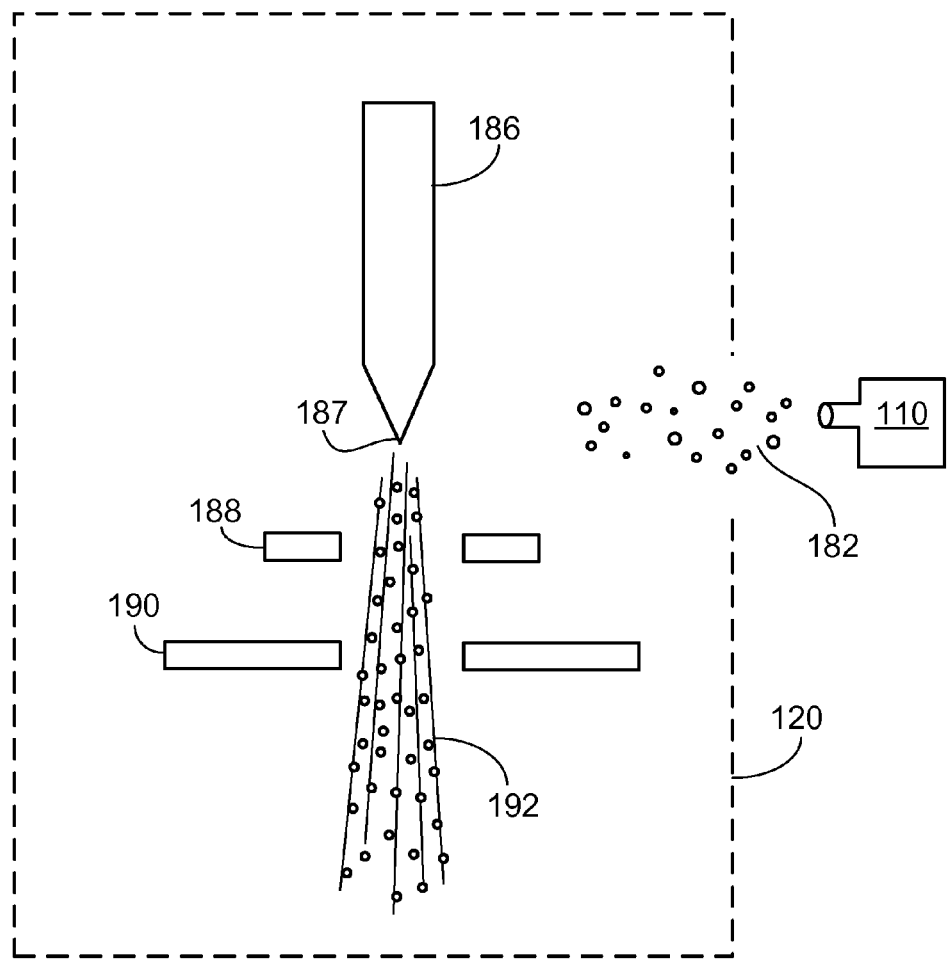
FIG. 16 is a schematic diagram of a gas field ion source.

As shown in FIG. 16, gas source 110 is configured to supply one or more gases 182 to gas field ion source 120. As described in more detail below, gas source 110 can be configured to supply the gas(es) at a variety of purities, flow rates, pressures, and temperatures. In general, at least one of the gases supplied by gas source 110 is a noble gas (helium (He), neon (Ne), argon (Ar), krypton (Kr), xenon (Xe)), and ions of the noble gas are desirably the primary constituent in ion beam 192. In general, as measured at surface 181 of sample 180, the current of ions in ion beam 192 increases monotonically as the pressure of the noble gas in system 100 increases. In certain embodiments, this relationship can be described by a power law where, for a certain range of noble gas pressures, the current increases generally in proportion to gas pressure. During operation, the pressure of the noble gas is typically $10^{-2}$ Torr or less (e.g., $10^{-3}$ Torr or less, $10^{-4}$ Torr or less), and/or $10^{-7}$ Torr or more (e.g., $10^{-6}$ Torr or more, $10^{-5}$ Torr or more) adjacent the tip apex (see discussion below). In general, it is desirable to use relatively high purity gases (e.g., to reduce the presence of undesirable chemical species in the system). As an example, when He is used, the He can be at least 99.99% pure (e.g., 99.995% pure, 99.999% pure, 99.9995% pure, 99.9999% pure). Similarly, when other noble gases are used (Ne gas, Ar gas, Kr gas, Xe gas), the purity of the gases is desirably high purity commercial grade.

Optionally, gas source 110 can supply one or more gases in addition to the noble gas(es). As discussed in more detail below, an example of such a gas is nitrogen. Typically, while the additional gas(es) can be present at levels above the level of impurities in the noble gas(es), the additional gas(es) still constitute minority components of the overall gas mixture introduced by gas source 110. As an example, in embodiments in which He gas and Ne gas are introduced by gas source 110 into gas field ion source 120, the overall gas mixture can include 20% or less (e.g., 15% or less, 12% or less) Ne, and/or 1% or more (e.g., 3% or more, 8% or more) Ne. For example, in embodiments in which He gas and Ne gas are introduced by gas source 110, the overall gas mixture can include from 5% to 15% (e.g., from 8% to 12%, from 9% to 11%) Ne. As another example, in embodiments in which He gas and nitrogen gas are introduced by gas source 110, the overall gas mixture can include 1% or less (e.g., 0.5% or less, 0.1% or less) nitrogen, and/or 0.01% or more (e.g., 0.05% or more) nitrogen. For example, in embodiments in which He gas and nitrogen gas are introduced by gas source 110, the overall gas mixture can include from 0.01% to 1% (e.g., from 0.05% to 0.5%, from 0.08 to 0.12%) nitrogen. In some embodiments, the additional gas(es) are mixed with the noble gas(es) before entering system 100 (e.g., via the use of a gas manifold that mixes the gases and then delivers the mixture into system 100 through a single inlet). In certain embodiments, the additional gas(es) are not mixed with the noble gas(es) before entering system 100 (e.g., a separate inlet is used for inputting each gas into system 100, but the separate inlets are sufficiently close that the gases become mixed before interacting with any of the elements in gas field ion source 120).

Gas field ion source 120 is configured to receive the one or more gases 182 from gas source 110 and to produce gas ions from gas(es) 182. Gas field ion source 120 includes an electrically conductive tip 186 with a tip apex 187, an extractor 190 and optionally a suppressor 188. Typically, the distance from tip apex 187 to surface 181 of sample 180 (not shown in FIG. 16) is five cm or more (e.g., 10 cm or more, 15 cm or more, 20 cm or more, 25 cm or more), and/or 100 cm or less (e.g., 80 cm or less, 60 cm or less, 50 cm or less). For example, in some embodiments, the distance from tip apex 187 to surface 181 of sample 180 is from five cm to 100 cm (e.g., from 25 cm to 75 cm, from 40 cm to 60 cm, from 45 cm to 55 cm).

Electrically conductive tip 186 can be formed of various materials. In some embodiments, tip 186 is formed of a metal (e.g., tungsten (W), tantalum (Ta), iridium (Ir), rhenium (Rh), niobium (Nb), platinum (Pt), molybdenum (Mo)). In certain embodiments, electrically conductive tip 186 can be formed of an alloy. In some embodiments, electrically conductive tip 186 can be formed of a different material (e.g., carbon (C)).

During use, tip 186 is biased positively (e.g., approximately 20 kV) with respect to extractor 190, extractor 190 is negatively or positively biased (e.g., from −20 kV to +50 kV) with respect to an external ground, and optional suppressor 188 is biased positively or negatively (e.g., from −5 kV to +5 kV) with respect to tip 186. Because tip 186 is formed of an electrically conductive material, the electric field of tip 186 at tip apex 187 points outward from the surface of tip apex 187. Due to the shape of tip 186, the electric field is strongest in the vicinity of tip apex 187. The strength of the electric field of tip 186 can be adjusted, for example, by changing the positive voltage applied to tip 186. With this configuration, un-ionized gas atoms 182 supplied by gas source 110 are ionized and become positively-charged ions in the vicinity of tip apex 187. The positively-charged ions are simultaneously repelled by positively charged tip 186 and attracted by negatively charged extractor 190 such that the positively-charged ions are directed from tip 186 into ion optics 130 as ion beam 192. Suppressor 188 assists in controlling the overall electric field between tip 186 and extractor 190 and, therefore, the trajectories of the positively-charged ions from tip 186 to ion optics 130. In general, the overall electric field between tip 186 and extractor 190 can be adjusted to control the rate at which positively-charged ions are produced at tip apex 187, and the efficiency with which the positively-charged ions are transported from tip 186 to ion optics 130.

As an example, without wishing to be bound by theory, it is believed that He ions can be produced as follows. Gas field ion source 120 is configured so that the electric field of tip 186 in the vicinity of tip apex 187 exceeds the ionization field of the un-ionized He gas atoms 182, and tip 186 is maintained at a relatively low temperature. When the un-ionized He gas atoms 182 are in close proximity to tip apex 187, the He atoms can be polarized by the electric field of the tip, producing a weakly attractive force between He atoms 182 and tip apex 187. As a result, He atoms 182 may contact tip apex 187 and remain bound (e.g., physisorbed) thereto for some time. In the vicinity of tip apex 187, the electric field is high enough to ionize He atoms 182 adsorbed onto tip apex 187, generating positively charged He ions (e.g., in the form of an ion beam).

In general, ion optics 130 are configured to direct ion beam 192 onto surface 181 of sample 180. As described in more detail below, ion optics 130 can, for example, focus, collimate, deflect, accelerate, and/or decelerate ions in beam 192. Ion optics 130 can also allow only a portion of the ions in ion beam 192 to pass through ion optics 130. Generally, ion optics 130 include a variety of electrostatic and other ion optical elements that are configured as desired. By manipulating the electric field strengths of one or more components (e.g., electrostatic deflectors) in ion optics 130, He ion beam 192 can be scanned across surface 181 of sample 180. For example, ion optics 130 can include two deflectors that deflect ion beam 192 in two orthogonal directions. The deflectors can have varying electric field strengths such that ion beam 192 is rastered across a region of surface 181.

When ion beam 192 impinges on sample 180, a variety of different types of particles 194 can be produced. These particles include, for example, secondary electrons, Auger electrons, secondary ions, secondary neutral particles, primary neutral particles, scattered ions and photons (e.g., X-ray photons, IR photons, visible photons, UV photons). Detectors 150 and 160 are positioned and configured to each measure one or more different types of particles resulting from the interaction between He ion beam 192 and sample 180. As shown in FIG. 15, detector 150 is positioned to detect particles 194 that originate primarily from surface 181 of sample 180, and detector 160 is positioned to detect particles 194 that emerge primarily from surface 183 of sample 180 (e.g., transmitted particles). As described in more detail below, in general, any number and configuration of detectors can be used in the microscope systems disclosed herein.

In some embodiments, multiple detectors are used, and some of the multiple detectors are configured to measure different types of particles. In certain embodiments, the detectors are configured to provide different information about the same type of particle (e.g., energy of a particle, angular distribution of a given particle, total abundance of a given particle). Optionally, combinations of such detector arrangements can be used.

In general, the information measured by the detectors is used to determine information about sample 180. Typically, this information is determined by obtaining one or more images of sample 180. By rastering ion beam 192 across surface 181, pixel-by-pixel information about sample 180 can be obtained in discrete steps. Detectors 150 and/or 160 can be configured to detect one or more different types of particles 194 at each pixel. Typically, a pixel is a square, although in some embodiments, pixels can have different shapes (e.g., rectangular). A pixel size, which corresponds to a length of a side of the pixel, can be, for example, from 100 pm to two μm (e.g., from one nm to one μm). In some embodiments, the location of adjacent pixels can be determined to within at least 200 pm (e.g., to within at least 100 pm, to within at least 75 pm, to within at least 50 pm). Thus, the operator of the system can determine the location of the center of the beam spot to within at least 200 pm (e.g., to within at least 100 pm, to within at least 75 pm, to within at least 50 pm). In certain embodiments, the field of view (FOV) of sample 180 is 200 nm or more (e.g., 500 nm or more, 1 µm or more, 50 µm or more, 100 µm or more, 500 µm or more, 1 mm or more, 1.5 mm or more), and/or 25 mm or less (15 mm or less, 10 mm or less, five mm or less). The field of view refers to the area of a sample surface that is imaged by the ion microscope.

The operation of microscope system 100 is typically controlled via electronic control system 170. For example, electronic control system 170 can be configured to control the gas(es) supplied by gas source 110, the temperature of tip 186, the electrical potential of tip 186, the electrical potential of extractor 190, the electrical potential of suppressor 188, the settings of the components of ion optics 130, the position of sample manipulator 140, and/or the location and settings of detectors 150 and 160. Optionally, one or more of these parameters may be manually controlled (e.g., via a user interface integral with electronic control system 170). Additionally or alternatively, electronic control system 170 can be used (e.g., via an electronic processor, such as a computer) to analyze the information collected by detectors 150 and 160 and to provide information about sample 180 (e.g., topography information, material constituent information, crystalline information, voltage contrast information, optical property information, magnetic information), which can optionally be in the form of an image, a graph, a table, a spreadsheet, or the like. Typically, electronic control system 170 includes a user interface that features a display or other kind of output device, an input device, and a storage medium.

Electronic control system 170 can also be configured to control operation of other devices in microscope system 100. For example, in some embodiments, electronic control system 170 can control heating of the sample by controlling operation of a laser source that is configured to heat the sample. Alternatively, or in addition, control system 170 can control operation of an electron source that is configured to heat the sample. As another alternative, or further in addition, control system 170 can control operation of a heating element (e.g., a resistive heating element) that can be used to heat the sample.

In certain embodiments, electronic control system 170 can be configured to control various properties of ion beam 192. For example, control system 170 can control a composition of ion beam 192 by regulating the flow of gases into gas field ion source 120. By adjusting various potentials in ion source 120 and ion optics 130, control system 170 can control other properties of ion beam 192 such as the position of the ion beam on sample 180, and the average energy of the incident ions.

In some embodiments, electronic control system 170 can be configured to control one or more additional particle beams. For example, in certain embodiments, one or more types of ion beam source and or electron beam sources can be present. Control system 170 can control each of the particle beam sources and their associated optical and electronic components.

Detectors 150 and 160 are depicted schematically in FIG. 15, with detector 150 positioned to detect particles from surface 181 of sample 180 (the surface on which the ion beam impinges), and detector 160 positioned to detect particles from surface 183 of sample 180. In general, a wide variety of different detectors can be employed in microscope system 200 to detect different particles, and a microscope system 200 can typically include any desired number of detectors. The configuration of the various detector(s) can be selected in accordance with particles to be measured and the measurement conditions. In some embodiments, a spectrally resolved detector may be used. Such detectors are capable of detecting particles of different energy and/or wavelength, and resolving the particles based on the energy and/or wavelength of each detected particles. In certain embodiments, a spectrally resolved detector includes components capable of directing particles to different regions of the detector based on the energy and/or wavelength of the particle.

Detection systems and methods are generally disclosed, for example, in U.S. patent application Ser. No. 11/600,711 entitled "ION SOURCES, SYSTEMS AND METHODS" by Billy W. Ward et al., filed on Nov. 15, 2006, now published as U.S. Publication No. U.S. 2007/0158558, the entire contents of which are incorporated herein by reference.

In general, detectors 150 and/or 160 can include any one or more of the following detector types: Everhart-Thornley (ET) detectors, which can be used to detect secondary electrons, ions, and/or neutral particles; microchannel plate detectors, which can be used to amplify a flux of secondary electrons, neutral atoms, or ions from a sample; conversion plates, which can be used to detect ions (e.g., scattered ions, secondary ions) from a sample or neutral particles (e.g., primary neutral He atoms) from the sample; channeltron detectors, which can be used to detect particles such as electrons, ions and neutral atoms leaving a sample; phosphor-based detectors, which include a thin layer of a phosphor material deposited atop a transparent substrate, and a photon detector such as a CCD camera, a PMT, or one or more diodes, and which can be used to detect electrons, ions and/or neutral particles from a sample; solid state detectors, which can be used to detect secondary electrons, ions, and/or neutral atoms from a sample; scintillator-based detectors, which include a scintillator material that generates photons in response to being struck by an incident particle (electron, ion, or neutral atom), which can be particularly useful for energy measurements of particles; electrostatic and magnetic prism detectors for ions and electrons; quadrupole detectors for ions; biased particle selectors for ions and electrons; time-of-flight detectors for secondary electrons, ions, and neutral atoms; and angle-resolving detectors that can measure angle-dependent scattering information for ions, electrons, and neutral atoms.

Computer Hardware and Software

In general, any of the analysis methods described above can be implemented in computer hardware or software, or a combination of both. The methods can be implemented in computer programs using standard programming techniques following the methods and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis methods can also be implemented as a computer-readable storage medium, configured with a computer program, where the storage medium so configured causes a computer to operate in a specific and predefined manner to perform the functions described herein.

OTHER EMBODIMENTS

Other embodiments are in the claims.

What is claimed is:

1. A method, comprising:
providing a sample comprising a material, the sample having a surface in a plane;
removing some of the material from the sample to form a channel which extends beneath the plane of the surface of the sample such that a first portion of the material of the sample is disposed above the channel and a second portion of the material of the sample is disposed below the channel, the channel having a single central axis defined by sidewalls of the channel which extend from the surface of the sample to a terminus of the channel, the sidewalls being symmetrically disposed around the single central axis, the channel extending one micron or more along the single central axis of the channel, and the single central axis of the channel being oriented at an angle to the surface of the sample;
after forming the channel, exposing a portion of the surface of the sample to a particle beam to cause particles to leave the surface of the sample; and
forming an image of the sample based on particles that leave the surface of the sample.

2. The method of claim 1, wherein the angle is 45 degrees or less.

3. The method of claim 1, wherein forming the channel comprises exposing the sample to a second particle beam that removes material from the sample.

4. The method of claim 3, wherein the second particle beam is a gallium ion beam.

5. The method of claim 1, further comprising adjusting an average energy of the particle beam so that particles that are incident on the portion of the sample pass through the sample and into the channel.

6. The method of claim 1, further comprising, prior to exposing the sample to the particle beam, forming a second channel in the sample, the second channel having sidewalls extending along a direction normal to the surface of the sample and having a maximum width in a direction parallel to the surface of the sample of one micron or less, wherein the exposed portion of the sample is positioned between the first and second channels.

7. The method of claim 6, wherein the maximum width of the second channel is 500 nm or less.

8. The method of claim 6, wherein exposing the portion of the sample to the particle beam comprises:
determining a side length $F \cdot \sqrt{A}$ of a smallest square that encloses the portion of the sample, wherein A is an area of the portion and F is a constant; and
exposing each of M regions of the portion of the sample to the particle beam, wherein each of the M regions is exposed continuously to the particle beam for a time period $t_1$, a shortest time period between successive exposures of any one of the M regions to the particle beam is $t_2$, and the time periods $t_1$ and $t_2$ are selected so that a ratio $$\frac{t_1}{t_1 + t_2}$$

is less than $$\frac{1}{2F\sqrt{M}}.$$

9. The method of claim 1, wherein the particle beam is an ion beam.

10. A method, comprising:
providing a sample comprising a material, the sample having a surface in a plane;
forming a channel that extends beneath the plane of the surface of the sample, wherein the channel extends along a direction normal to the plane of the surface of the sample, wherein a maximum width of the channel measured in a direction parallel to the plane of the surface of the sample is one micron or less, and wherein the channel substantially surrounds a portion of the sample in the plane of the surface of the sample;
after forming the channel, exposing the surface of the portion of the sample to a particle beam to cause particles to leave the surface of the portion the sample; and
forming an image of the portion of the sample based on particles that leave the surface of the portion of the sample.

11. The method of claim 10, wherein exposing the portion of the sample to the particle beam comprises:
determining a side length $F \cdot \sqrt{A}$ of a smallest square that encloses the portion of the sample, wherein A is an area of the portion and F is a constant; and
exposing each of M regions of the portion of the sample to the particle beam, wherein each of the M regions is exposed continuously to the particle beam for a time period $t_1$, a shortest time period between successive exposures of any one of the M regions to the particle beam is $t_2$, and the time periods $t_1$ and $t_2$ are selected so that a ratio $$\frac{t_1}{t_1 + t_2}$$

is less than $$\frac{1}{2F\sqrt{M}}.$$

12. The method of claim 10, wherein the particle beam is an ion beam.

13. A method, comprising:
providing a sample comprising a material, the sample having a surface in a plane;
forming a plurality of channels that extend beneath the plane of the surface of the sample, wherein each of the plurality of channels extends along a direction normal to the plane of the surface of the sample, wherein a maximum width of each of the plurality of channels measured in a direction parallel to the plane of the surface of the sample is one micron or less, and wherein the plurality of channels are positioned to substantially surround a portion of the sample in the plane of the surface of the sample;
after forming the plurality of channels, exposing the surface of the portion of the sample to a particle beam to cause particles to leave the surface of the portion of the sample; and
forming an image of the sample based on particles that leave the surface of the portion of the sample.

14. The method of claim 13, wherein the particle beam is an ion beam.

15. A method, comprising:
providing a sample comprising a material, the sample having a surface in a plane;
forming first and second channels that extend beneath the plane of the surface of the sample, the first channel having a single central axis defined by sidewalls of the channel which extend from the surface of the sample to a terminus of the channel, the sidewalls being symmetrically disposed around the single central axis, the single central axis of the first channel extending along a direction oriented at an angle relative to the plane of the surface of the sample, the second channel extending along a direction normal to the plane of the surface of the sample and having a maximum width in a direction parallel to the plane of the surface of the sample of one micron or less;
after forming the first and second channels, directing a particle beam to be incident on a portion of the surface of the sample to cause particles to leave the second surface, the portion of the surface of the sample being positioned between the first and second channels; and
forming an image of the sample based on particles that leave the portion of the surface.

16. The method of claim 15, wherein the particle beam is an ion beam.

17. A method, comprising:
using a gas field ion source to form a particle beam comprising $^3He^+$ ions and $^4He^+$ ions, a ratio of the $^3He^+$ ions in the particle beam to the $^4He^+$ ions in the particle beam being at least 0.05;
exposing a sample to the particle beam comprising $^3He^+$ ions to cause particles to leave a surface of the sample; and
forming an image of the sample based on particles that leave the surface.

18. The method of claim 17, wherein exposing the sample to the particle beam comprises:
determining a side length $F \cdot \sqrt{A}$ of a smallest square that encloses a portion of the sample, wherein A is an area of the portion and F is a constant; and
exposing each of M regions of the portion of the sample to the particle beam, wherein each of the M regions is exposed continuously to the particle beam for a time period $t_1$, a shortest time period between successive exposures of any one of the M regions to the particle beam is $t_2$, and the time periods $t_1$ and $t_2$ are selected so that a ratio $$\frac{t_1}{t_1 + t_2}$$

is less than $$\frac{1}{2F\sqrt{M}}.$$

19. The method of claim 17, further comprising, before exposing the sample to the particle beam, forming a channel in the sample, the channel extending along a direction oriented at an angle to the surface, so that exposing the sample to the particle beam comprises exposing a portion of the sample above the channel to the particle beam.

20. The method of claim 19, further comprising adjusting an average energy of the particle beam so that particles that are incident on the portion of the sample pass through the sample and into the channel.

21. A method, comprising:
exposing a sample to a particle beam to cause particles to leave a surface of the sample, and forming an image frame based on particles that leave the surface;
repeating the exposing and detecting to form a plurality of image frames so that the sample is damaged;
for each of the plurality of image frames, determining an estimate of accumulated sample damage and a weighting value based on the estimate of the accumulated sample damage; and
combining the plurality of image frames to form an image of the sample, wherein the image frames are combined according to the weighting value determined for each image frame.

22. The method of claim 21, wherein the particle beam is an ion beam.

23. The method of claim 15, further comprising:
exposing the surface of the sample to the particles so that at least some of the particles pass through a portion of the sample and enter the first channel.

24. A method, comprising:
forming a channel in a sample, the channel extending beneath a plane containing a surface of the sample;
after forming the channel exposing the surface of a sample to a particle beam to cause particles to leave the surface of the sample;
forming an image of the sample based on particles that leave the surface; and
using a heat source to heat the sample during the exposure to the particle beam, the heat source being different from the particle beam.

25. The method of claim 24, wherein the particle beam is an ion beam.

* * * * *

UNITED STATES PATENT AND TRADEMARK OFFICE
CERTIFICATE OF CORRECTION

| | | |
|---|---|---|
| PATENT NO. | : 8,907,277 B2 | Page 1 of 1 |
| APPLICATION NO. | : 12/919676 | |
| DATED | : December 9, 2014 | |
| INVENTOR(S) | : Rainer Knippelmeyer et al. | |

It is certified that error appears in the above-identified patent and that said Letters Patent is hereby corrected as shown below:

In the Specification

Col. 3, line 7, delete ". For" and insert -- For --.

Col. 8, line 64, delete "Tumult" and insert -- Terrault --.

Col. 12, line 31, delete "the the" and insert -- the --.

Col. 19, line 51, delete "and or" and insert -- and/or --.

In the Claims

Col. 21, line 47, Claim 8, delete "claim 6" and insert -- claim 1 --.

Signed and Sealed this
Fourteenth Day of April, 2015

Michelle K. Lee
*Director of the United States Patent and Trademark Office*